US010172645B2

(12) United States Patent
Zeetser et al.

(10) Patent No.: US 10,172,645 B2
(45) Date of Patent: Jan. 8, 2019

(54) METHOD OF CORRECTING HALLUX VARUS JOINT DEFORMITY

(71) Applicant: FastForward Surgical Inc., Henderson, NV (US)

(72) Inventors: Vladimir Zeetser, Tarzana, CA (US); Dawn Buratti, Malibu, CA (US)

(73) Assignee: FastForward Surgical Inc., Henderson, NV (US)

( * ) Notice: Subject to any disclaimer, the term of this patent is extended or adjusted under 35 U.S.C. 154(b) by 274 days.

(21) Appl. No.: 15/161,075

(22) Filed: May 20, 2016

(65) Prior Publication Data
US 2017/0333101 A1 Nov. 23, 2017

(51) Int. Cl.
*A61B 17/56* (2006.01)
*A61B 17/84* (2006.01)
*A61B 17/86* (2006.01)
*A61B 17/04* (2006.01)
(Continued)

(52) U.S. Cl.
CPC .......... *A61B 17/56* (2013.01); *A61B 17/0401* (2013.01); *A61B 17/0482* (2013.01); *A61B 17/1682* (2013.01); *A61B 17/842* (2013.01); *A61B 17/8645* (2013.01);
(Continued)

(58) Field of Classification Search
CPC .......... A61B 17/0401; A61B 2017/044; A61B 17/56; A61B 2017/564; A61B 2017/565; A61B 17/842; A61B 17/8645
See application file for complete search history.

(56) References Cited

U.S. PATENT DOCUMENTS 1,665,030 A    4/1928   Hartwig
1,746,865 A    2/1930   Page
2,596,038 A    5/1952   Mayer
(Continued)

FOREIGN PATENT DOCUMENTS

CN          105828732 A    8/2016
WO    WO 2008/019511 A1    2/2008
(Continued)

OTHER PUBLICATIONS

International Search Report and Written Opinion in Application No. PCT/US2013/050687, dated Sep. 6, 2013, 14 pages.
(Continued)

*Primary Examiner* — Larry E Waggle, Jr.
(74) *Attorney, Agent, or Firm* — Knobbe, Martens, Olson & Bear LLP

(57) ABSTRACT

Disclosed are methods for correcting hallux varus joint deformity in a foot. The method can include forming a first hole in a first metatarsal of the foot from a medial side to a lateral side of the first metatarsal. A second hole can be formed in a proximal phalanx of a hallux that extends from a medial side to a lateral side of the proximal phalanx. The method includes passing a suture through the first hole, along a lateral side of a first metatarsal phalangeal joint, and through the second hole. The suture can be tensioned between the first and second holes to reduce the hallux to a rectus position relative to the first metatarsal. The suture can be secured within the first and second holes with a first interference screw inserted within the first hole and a second interference screw inserted within the second hole.

8 Claims, 19 Drawing Sheets

(51) Int. Cl.
 *A61B 17/16* (2006.01)
 *A61B 17/88* (2006.01)
(52) U.S. Cl.
 CPC ..... *A61B 17/8875* (2013.01); *A61B 2017/044* (2013.01); *A61B 2017/564* (2013.01); *A61B 2017/565* (2013.01)

(56) References Cited

U.S. PATENT DOCUMENTS

| | | | |
|---|---|---|---|
| 2,706,023 A | 4/1955 | Merritt | |
| 2,958,324 A | 11/1960 | Berkemann | |
| 4,583,303 A | 4/1986 | Laiacona et al. | |
| 4,644,940 A | 2/1987 | Nakamura | |
| 5,190,545 A | 3/1993 | Corsi et al. | |
| 5,222,977 A | 6/1993 | Esser | |
| 5,282,782 A | 2/1994 | Kasahara | |
| 5,529,075 A | 6/1996 | Clark | |
| 5,743,913 A | 4/1998 | Wellisz | |
| 5,843,085 A | 12/1998 | Graser | |
| 6,318,373 B1 | 11/2001 | Kasahara | |
| 6,391,031 B1 | 5/2002 | Toomey | |
| 6,520,965 B2 | 2/2003 | Chervitz et al. | |
| 6,629,943 B1 | 10/2003 | Schroder | |
| 6,746,450 B1 | 6/2004 | Wall et al. | |
| 6,964,645 B1 | 11/2005 | Smits | |
| 7,344,538 B2 | 3/2008 | Myerson et al. | |
| 7,582,088 B2 | 9/2009 | Marissen et al. | |
| 7,875,058 B2 | 1/2011 | Holmes | |
| 7,901,431 B2 | 3/2011 | Shumas | |
| 8,057,522 B2 | 11/2011 | Rothman et al. | |
| 8,221,455 B2 | 7/2012 | Shumas | |
| 8,257,403 B2 | 9/2012 | Den Hartog et al. | |
| 8,257,406 B2 | 9/2012 | Kay et al. | |
| 8,398,678 B2 | 3/2013 | Baker et al. | |
| 8,821,551 B2 | 9/2014 | Zeetser et al. | |
| 8,998,904 B2 | 4/2015 | Zeetser et al. | |
| 2004/0127907 A1 | 7/2004 | Dakin et al. | |
| 2005/0021033 A1 | 1/2005 | Zeiler et al. | |
| 2005/0049593 A1 | 3/2005 | Duong et al. | |
| 2006/0241607 A1 | 10/2006 | Myerson et al. | |
| 2006/0241608 A1 | 10/2006 | Myerson et al. | |
| 2008/0008777 A1 | 1/2008 | Radovic | |
| 2008/0155731 A1 | 7/2008 | Kasahara | |
| 2008/0177302 A1 | 7/2008 | Shurnas | |
| 2008/0269806 A1 | 10/2008 | Zhang et al. | |
| 2009/0036893 A1 | 2/2009 | Kartalian et al. | |
| 2009/0076617 A1 | 3/2009 | Ralph et al. | |
| 2009/0210010 A1 | 8/2009 | Strnad et al. | |
| 2009/0222047 A1 | 9/2009 | Graham | |
| 2009/0254190 A1 | 10/2009 | Gannoe et al. | |
| 2010/0036430 A1 | 2/2010 | Hartdegen et al. | |
| 2010/0094294 A1 | 4/2010 | Gillard et al. | |
| 2010/0094428 A1 | 4/2010 | Ralph et al. | |
| 2010/0106110 A1 | 4/2010 | De Luca | |
| 2010/0125297 A1 | 5/2010 | Guederian et al. | |
| 2010/0152752 A1 | 6/2010 | Denove et al. | |
| 2010/0211071 A1 | 8/2010 | Lettmann et al. | |
| 2010/0211075 A1 | 8/2010 | Stone | |
| 2010/0234896 A1 | 9/2010 | Lorenz et al. | |
| 2010/0249687 A1 | 9/2010 | Goswami et al. | |
| 2010/0262194 A1 | 10/2010 | Wagner et al. | |
| 2011/0224729 A1 | 2/2011 | Baker | |
| 2011/0061664 A1 | 3/2011 | Paris Mayans Carlos | |
| 2011/0077656 A1 | 3/2011 | Sand et al. | |
| 2011/0082405 A1 | 4/2011 | Domangue et al. | |
| 2011/0118780 A1 | 5/2011 | Holmes, Jr. | |
| 2011/0119807 A1 | 5/2011 | DellaCorte et al. | |
| 2011/0130789 A1 | 6/2011 | Shurnas et al. | |
| 2011/0178557 A1 | 7/2011 | Rush et al. | |
| 2011/0301648 A1 | 12/2011 | Lofthouse et al. | |
| 2012/0016426 A1 | 1/2012 | Robinson | |
| 2012/0016428 A1* | 1/2012 | White | A61B 17/0401 606/86 R |
| 2012/0071935 A1 | 3/2012 | Keith et al. | |
| 2012/0215147 A1 | 8/2012 | Lunnon | |
| 2012/0330322 A1 | 12/2012 | Sand et al. | |
| 2015/0282849 A1 | 10/2015 | Zeetser et al. | |
| 2015/0313655 A1 | 11/2015 | Zeetser et al. | |
| 2016/0157904 A1 | 6/2016 | Zeetser et al. | |

FOREIGN PATENT DOCUMENTS

| | | |
|---|---|---|
| WO | WO 2009/086397 A2 | 7/2009 |
| WO | WO 2014/014914 | 1/2014 |
| WO | WO 2015/009808 | 1/2015 |

OTHER PUBLICATIONS

International Search Report and Written Opinion in Application No. PCT/US2014/046824 dated Nov. 24, 2014 in 13 pages.
Extended Search Report in Application EP 14825755 dated Jan. 17, 2017 in 7 pages.
Arthrex, Hallux Varus Repair Utilizing InternalBrace™ Augmentation, http://www.arthex.com/resources/video/OL7qlPIYh0yivwFT8USsLA/hallux-varus-repair-utilizing-internalbrace-augmentation, last revised on Apr. 7, 2016. Applicants have not enclosed the video at the URL link provided. However, if the Examiner cannot readily access the video at the above-link, Applicants would be pleased to provide the video at any time upon request.

* cited by examiner

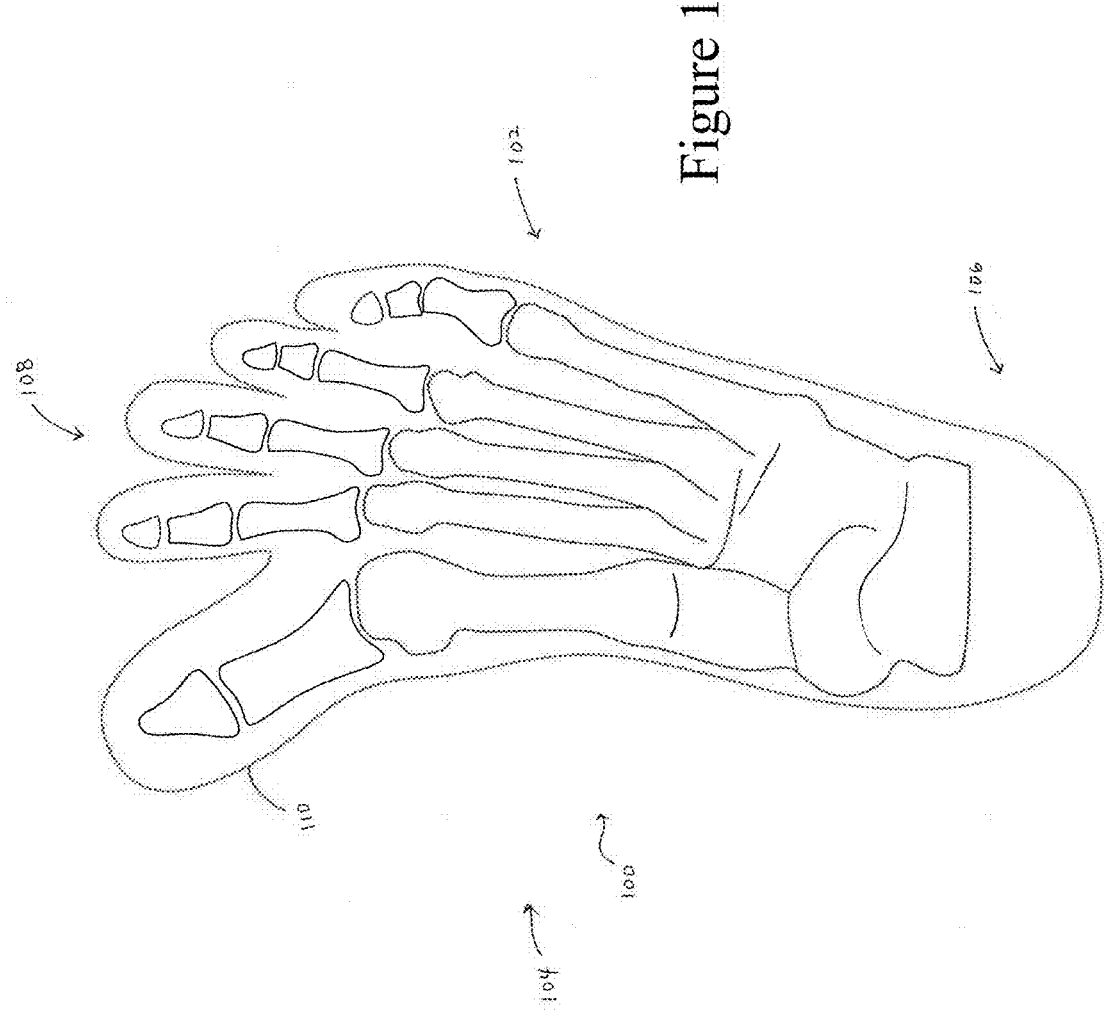

METHOD OF CORRECTING HALLUX VARUS JOINT DEFORMITY

BACKGROUND

Field

The present disclosure relates to medical systems, methods, and kits for the correction of hallux varus joint deformity in a foot. In one embodiment, the disclosure is directed to treating hallux varus, a condition in which the big toe deviates away from the second toe medially toward the midline of the body.

Description of the Related Art

Hallux varus is a condition in which the hallux—the big toe—begins to deviate away from the second toe, medially toward the midline of the body. This can create an angular deformity between the big toe and the first metatarsal, with which it articulates. Hallux varus has variable degrees of severity, symptomatology, and etiology.

Causes can include, for example: iatrogenic postoperative (overcorrection of hallux valgus), idiopathic, rheumatic, and post traumatic (tear of the hallux lateral collateral ligament). Flexible hallux varus is a common finding where the hallux appears straight until the foot becomes weight bearing at which time it deviates medially. Traumatic hallux varus may occur following sports injuries, secondary to rupture of the lateral collateral ligament and conjoined tendon. Acquired hallux varus may be idiopathic, occurring without prior injury or surgery. Medial deviation of the hallux can become progressively more severe and cause problems with wearing closed shoes. Furthermore, as the hallux progressively moves medially, the second digit often follows with medial deviation to occupy the space.

SUMMARY

Disclosed herein in one embodiment is a method of reducing, repairing and/or correcting hallux varus. In some embodiments, the method can include the use of suture tape and a plurality of interference screws which may be made out of PEEK or other material. As will be described in more detail below, the method can realign the first metatarsal phalangeal joint by first fixating the suture tape within the proximal phalanx using a threaded interference screw which engages both the medial and lateral cortices. In some embodiments, the method then includes tensioning the suture tape which is placed longitudinally along the lateral aspect of the joint. The method can then include fixating the other end of the suture tape within the first metatarsal using a second fully threaded interference screw which engages both the medial and lateral cortices.

In some embodiments, a method of correcting hallux varus joint deformity can include forming a first hole in a first metatarsal of the foot, wherein the first hole extends from a medial side of the first metatarsal to a lateral side of the first metatarsal. The method can also include forming a second hole in a proximal phalanx of a hallux of the foot, wherein the second hole extends from a medial side of the proximal phalanx to a lateral side of the proximal phalanx. In some examples, the method includes passing a suture through the first hole, along a lateral side of a first metatarsal phalangeal joint, and through the second hole. In some embodiments, the method includes securely fixating the suture within the first hole and the second hole with a first interference screw inserted within the first hole and a second interference screw inserted within the second hole. In some embodiments, the suture is tensioned between the first and second holes to reduce the hallux to a rectus position relative to the first metatarsal.

In some embodiments, the first hole is formed before the second hole. In other embodiments, the suture is passed first through the first hole and then through the second hole. In other embodiments, the method can comprise using one or more suture passers to pass the suture through the first hole, along a lateral side of a first metatarsal phalangeal joint, and through the second hole. In other embodiments, the interference screws extend in a medial-to-lateral direction through the first and second holes, with threads of the first and second interference screws engaging medial and lateral cortices of the first metatarsal and the proximal phalanx, respectively.

In some embodiments, a method of correcting hallux varus joint deformity can include making a first incision medial or dorsomedial to a first metatarsal phalangeal joint. The method can include making a second incision between a hallux and a second toe of the foot, wherein the second incision is lateral to the first metatarsal phalangeal joint. In some embodiments, the method can include driving a guidewire into a medial side of a first bone on a first side of the first metatarsal phalangeal joint, wherein the guidewire is driven from the medial side to the lateral side of the first bone. In some examples, the first bone is either a first metatarsal and the guidewire is driven through the metatarsal neck, or the first bone is a proximal phalanx of the hallux. In some examples, the method can include drilling a first hole along the guidewire to form a medial to lateral hole in the medial side of the first bone. In some embodiments, the hole is formed using a 4.00 mm cannulated drill. In some embodiments, the method can include driving a guidewire into a medial side of a second bone on a second side of the first metatarsal phalangeal joint, wherein the guidewire is driven from the medial side to the lateral side of the second bone. In some examples, the second bone is either a first metatarsal and the guidewire is driven through the metatarsal neck, or the second bone is a proximal phalanx of the hallux, the second bone being different from the first bone. The method can include drilling a second hole along the guidewire to form a medial to lateral hole in the medial side of the second bone. In some embodiments, the hole is formed using a 4.00 mm cannulated drill. In some examples, the method can include tapping the first and second hole with a 4.75 mm tap. In some embodiments, the method can include threading a suture passer through the first hole, wherein the suture passer retains a suture tape such that the suture tape is pulled through the first hole. In some examples, the suture passer is threaded from the medial side to the lateral side of the first bone. In some examples, the method can include pulling the suture passer and the attached suture tape along a lateral side of the first metatarsal phalangeal joint to the second hole. In some embodiments, the method can include threading the suture passer through the second hole from the medial side to the lateral side of the second bone, and pulling the suture tape using the suture passer through the second hole from the lateral side to the medial side. In some embodiments, the method can include tensioning the suture tape such that the suture tape is placed longitudinally along the lateral side of the metatarsal phalangeal joint. The method can include threading a first interference screw into either the first hole or the second hole to securely fixate the suture tape within either the first hole or the second hole. In some examples, the first interference screw is driven from the medial end to the lateral end of the hole with screw threads engaging both medial and lateral cortices. In some embodiments, the first interference screw is a 4.75 mm interference screw. In some examples, the method can include reducing the hallux to a rectus position relative to the first metatarsal. In some embodiments, the method can include threading a second interference screw into the other of the first hole or the second hole to securely fixate the suture tape within the second of the first hole or the second hole while maintaining tension on the suture tape. In some embodiments, the second interference screw is driven from the medial end to the lateral end of the hole, wherein the second interference screw is a 4.75 mm interference screw. In some embodiments, the method can include removing the remaining ends of the suture tape.

In some embodiments, disclosed is a kit for treating hallux varus joint deformity that comprises suture tape and at least two interference screws. In some examples, the kit can include a suture passer configured to retain the suture tape and pass the suture tape through holes in a first metatarsal and a proximal phalanx of the foot. In some embodiments, the interference screws are sized and configured to retain the suture tape under tension within the holes in the first metatarsal and the proximal phalanx.

In other embodiments, the kit can include a cannulated bone drill configured to drill a 4.00 mm hole through a bone in the foot. In other embodiments, the kit can include a bone tap. In other embodiments, the kit comprises a pair of PEEK interference screws. In other embodiments, the kit comprises a pair of 4.75 mm interference screws. In other embodiments, the kit comprise interference screws that have screw threads configured to engage medial and lateral corticies of the first metatarsal and the proximal phalanx.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 1 shows a superior-anterior cross-sectional view of a foot with hallux varus.

DETAILED DESCRIPTION

Hallux varus is a condition in which the big toe begins to deviate away from the second toe, medially toward the midline of the body. As illustrated in FIG. 1, this can create an angular deformity between the big toe and the first metatarsal, with which it articulates.

Historically, hallux varus correction may include non-surgical and surgical methods. Non-surgical treatments include dynamic splinting or taping of the angular deformity, which has limited use. Surgical procedures are divided into soft tissue and bone. Soft tissue procedures include capsulotomies and tendon transfers which also yield limited results. Bone procedures include osteotomies of the first metatarsal or fusion of the first metatarsal phalangeal joint. Another procedure described for reduction of hallux varus uses a button-suture-button construct, in which the buttons are located medial to the proximal phalanx and first metatarsal and the suture is passed along the lateral aspect of the metatarsal phalangeal joint.

Overview

Disclosed is a method of reducing, repairing and/or correcting hallux varus. In some embodiments, the method can include the use of suture tape and a plurality of interference screws. As will be described in more detail below, in some embodiments the method realigns the first metatarsal phalangeal joint by first fixating the suture tape within the proximal phalanx using a fully threaded PEEK interference screw which engages both the medial and lateral cortices. In some embodiments, the method can include tensioning the suture tape which is placed longitudinally along the lateral aspect of the joint. In some examples, the method can include fixating the other end of the suture tape within the first metatarsal using a second fully threaded PEEK interference screw which engages both the medial and lateral cortices.

The present disclosure provides a number of anatomical directional references. For the purpose of this application, the term "proximal" and "distal" are used to describe parts of a feature that are close to or distant from the center of the body. For example, the upper arm is "proximal" while the hand is "distal." The term "lateral" is used to refer to the sides of the body, while the term "medial" is used to refer to structures close to the center of the body.

For example, with regard to the foot, the side of the foot containing the big toe is the medial side 104 while the side of the foot containing the pinky toe is the lateral side 102. As well, the distal end 108 of the foot is the end of the foot closer to the toes, while the proximal end 106 of the foot is closer to the heel of the foot.

Methods for the Treatment of Hallux Varus

Figure 2A:
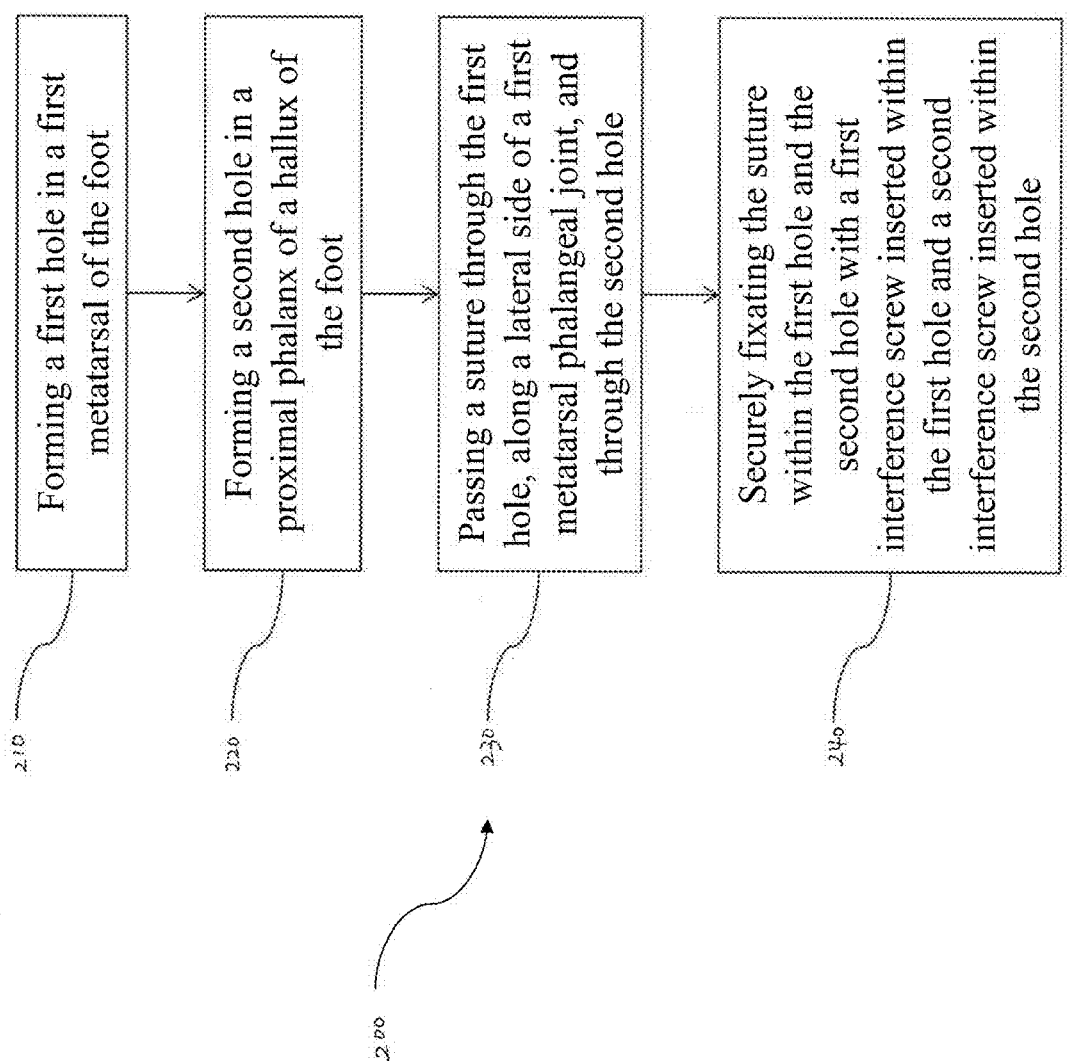
FIG. 2A illustrates a flow chart of an embodiment of a method for the treatment of hallux varus.
Figure 2B:
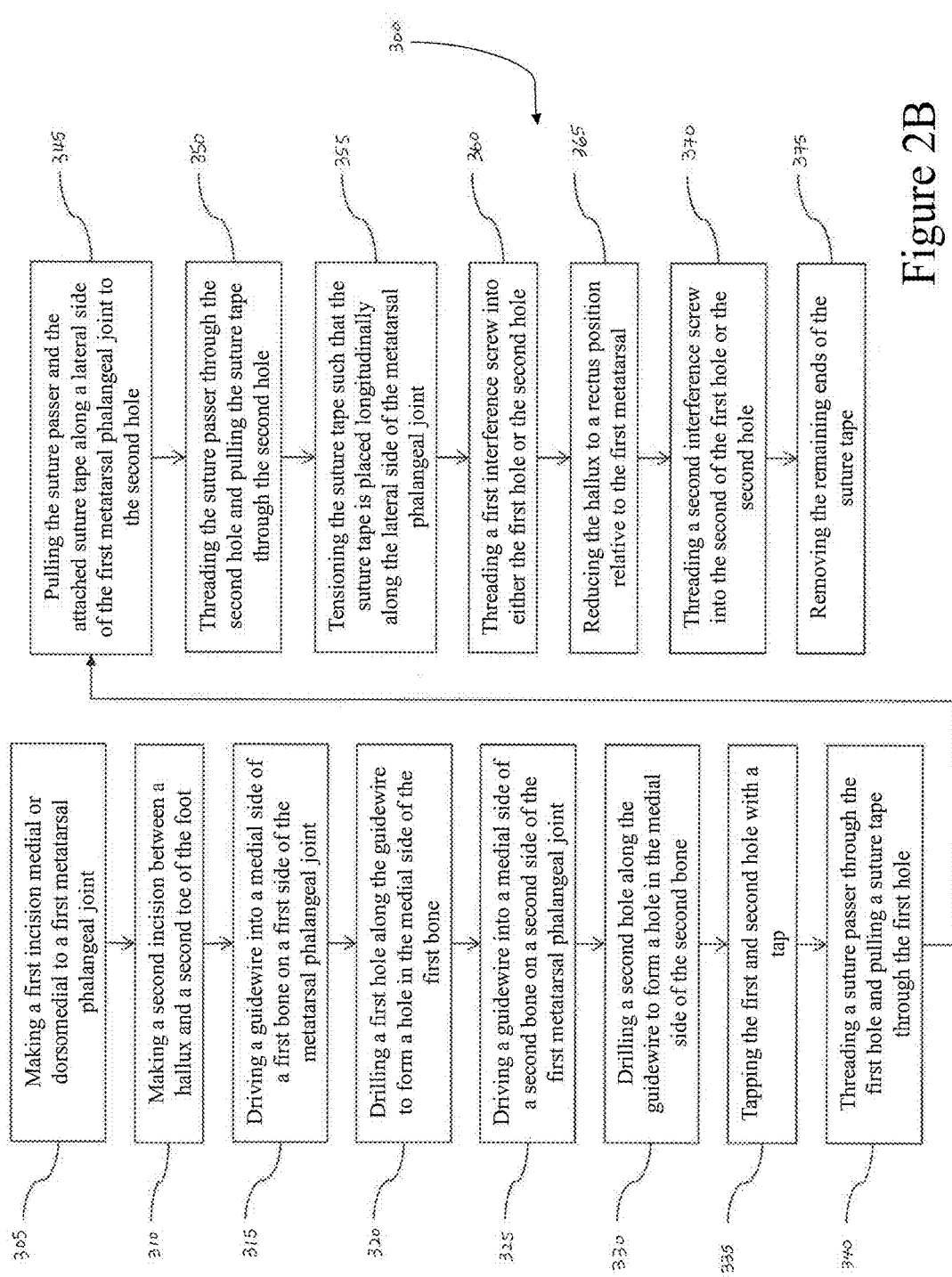
FIG. 2B illustrates a flow chart of another embodiment of a method for the treatment of hallux varus.
Figure 3:
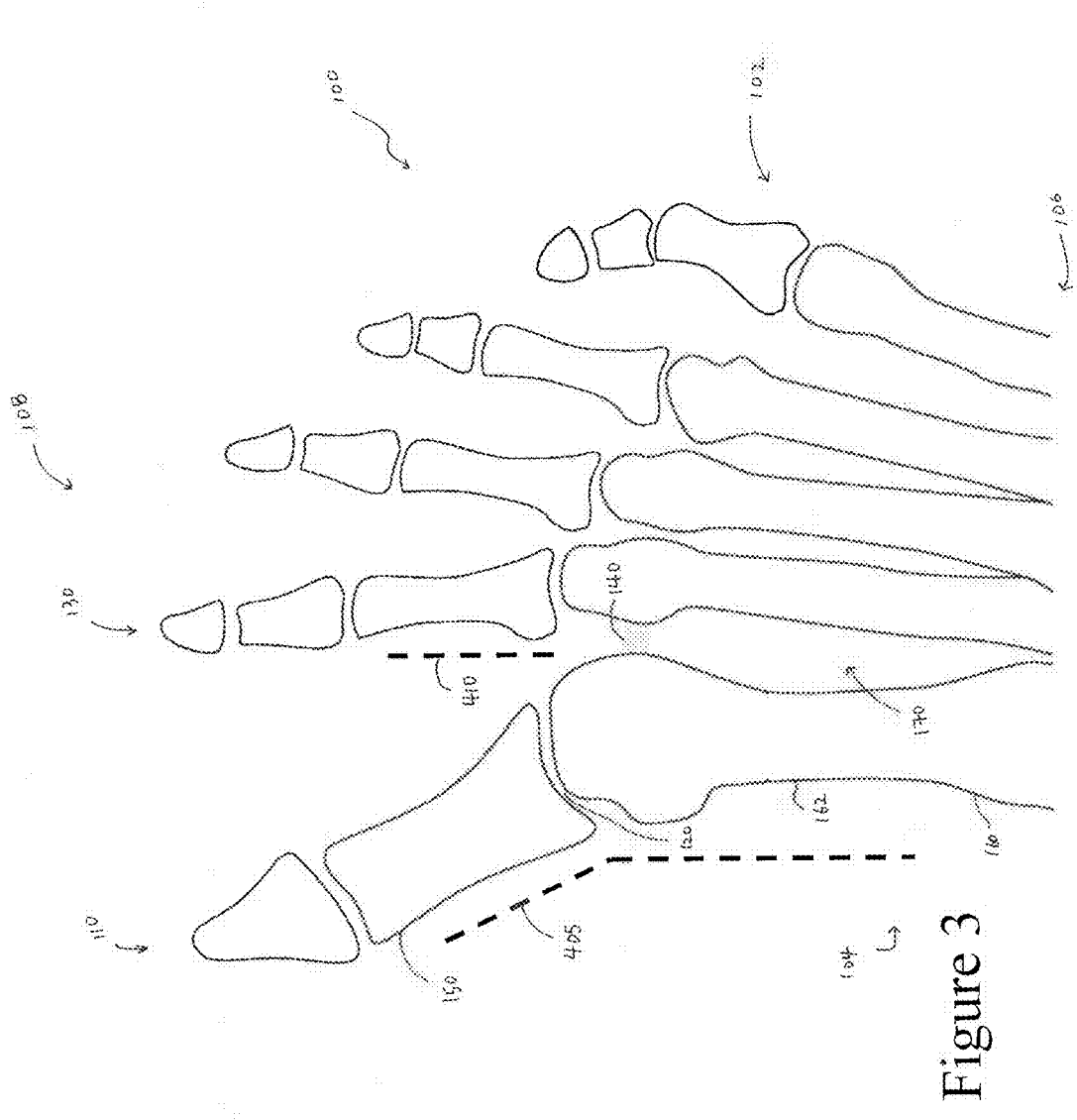
FIG. 3 illustrates a top view of the superior-anterior cross-sectional view of a foot with hallux varus, illustrating the location of the incisions in the foot.

FIGS. 2A-2B illustrates flow charts of methods for treating hallux varus. Turning first to FIG. 2B, the flow chart illustrates a method for treating hallux varus 300. In some embodiments, the method for treating hallux varus 300 can include block 305 which describes making a first incision that is medial or dorsomedial to a first metatarsal phalangeal joint. The step described in block 305 is illustrated in FIG. 3. As shown in FIG. 3, the foot 100 includes a hallux varus 110 that is deviated from the second toe. In some embodiments, a first medial or dorsomedial incision 405 is made over the first metatarsal phalangeal joint 120. In some examples, the dissection is carried down to the first metatarsal phalangeal joint 120 and a capsular incision can be made to fully expose, and release, the joint medially.

In some embodiments, the method for treating hallux varus 300 can include block 310 which describes making a second incision between a hallux and a second toe of the foot. As illustrated in FIG. 3, the second incision 410 can be made between the hallux varus 110 and the second toe 130. In some embodiments, the second incision 410 can be lateral to the first metatarsal phalangeal joint 120. In some examples, the lateral joint ligament 140 and the joint capsule are left intact.

Although the method for treating hallux varus 300 identifies the first incision 405 as a medial or dorsomedial incision to the first metatarsal phalangeal joint and the second incision 410 as between the hallux varus 110 and the second toe 130, the order that the incisions are made is not important and the second incision 410 can be made first and the first incision 405 made second. Other incision locations may also be used.

In some examples, the method for treating hallux varus 300 can include block 315 that describes driving a guidewire into a medial side of a first bone on a first side of the metatarsal phalangeal joint. In some embodiments, the guidewire (not illustrated) is driven into the medial side 104 of the first metatarsal neck 162. In some examples, the guidewire is driven in a direction from the medial side 104 to the lateral side 102 such that the guidewire enters from the medial side 104 of the first metatarsal neck 162 and exits from the lateral side 102 of the first metatarsal neck 162.

Figure 4:
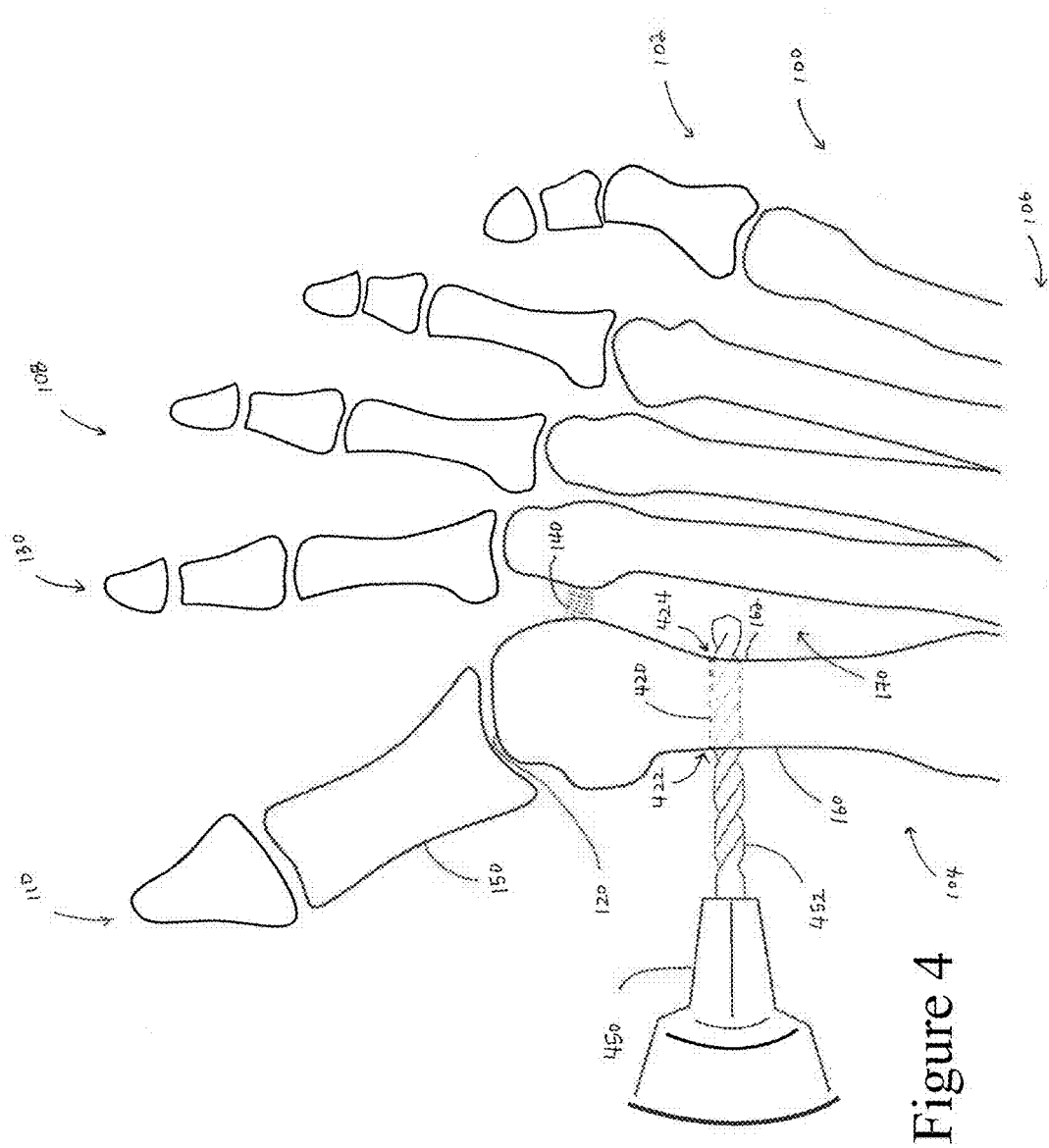
FIG. 4 illustrates a top view of the superior-anterior cross-sectional view of the foot with hallux varus of FIG. 3, illustrating the location of the drilling of a first hole in the foot as discussed in FIGS. 2A-2B.

In some embodiments, the method for treating hallux varus 300 can include block 320 that describes drilling a first hole along the guidewire to form a hole in the medial side of the first bone. As shown in FIG. 4, in some embodiments, a cannulated drill 450 with a drill bit 452 can be placed over the guidewire (not illustrated) so as to drill a first hole 420 through the first metatarsal neck 162 of the first metatarsal 160. In some examples, the first hole 420 is drilled from a medial end 422 to a lateral end 424. In some embodiments a 4.0 mm cannulated drill is used.

In some examples, the method for treating hallux varus 300 can include block 325 that describes driving a guidewire into a medial side of a second bone on a second side of the metatarsal phalangeal joint. In some embodiments, the guidewire (not illustrated) is driven into the medial side 104 of the proximal phalanx 150. In some examples, the guidewire is driven in a direction from the medial side 104 to the lateral side 102 such that the guidewire enters from the medial side 104 of the proximal phalanx 150 and exits from the lateral side 102 of the proximal phalanx 150.

Figure 5:
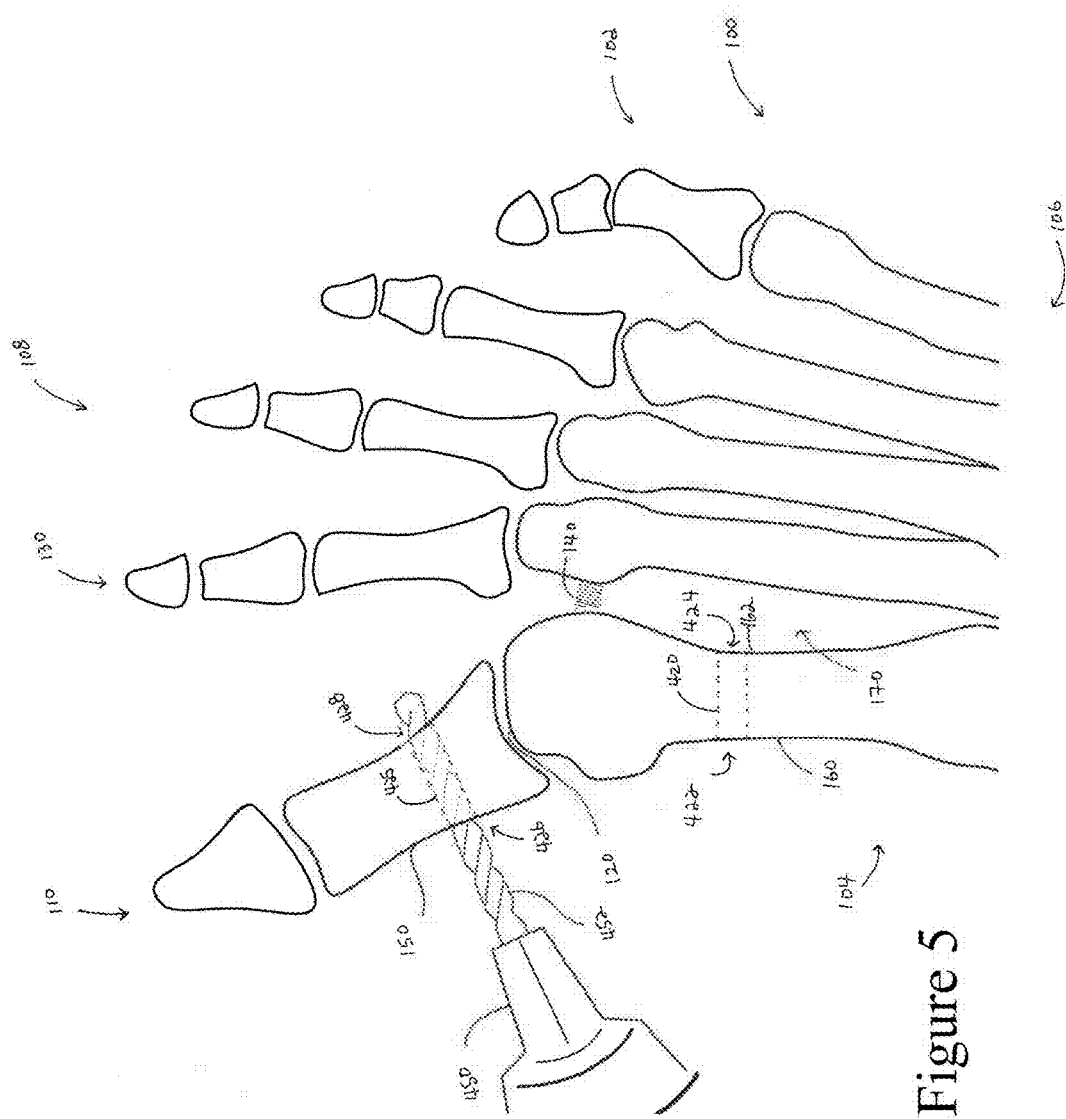
FIG. 5 illustrates a top view of the superior-anterior cross-sectional view of the foot with hallux varus of FIGS. 3-4, illustrating the location of the drilling of a second hole in the foot.

In some embodiments, the method for treating hallux varus 300 can include block 330 that describes drilling a second hole along the guidewire to form a hole in the medial side of the second bone. As shown in FIG. 5, in some examples, a cannulated drill 450 with a drill head 452 can be placed over the guidewire (not illustrated) so as to drill a second hole 425 through the proximal phalanx 150. In some embodiments, the second hole 425 is drilled from a medial end 426 to a lateral end 428. In some embodiments a 4.00 mm cannulated drill is used.

Although the method for treating hallux varus 300 identifies the first hole 420 as going through the first metatarsal neck 162 of the first metatarsal 160 and the second hole 425 as going through the proximal phalanx 150, the order of the holes drilled is not important and the first hole 420 can instead be made in the proximal phalanx 150 and the second hole 425 can instead be made in the first metatarsal neck 162 of the first metatarsal 160.

In some examples, the method for treating hallux varus 300 can include block 335 that describes tapping the first hole 420 and second hole 425 with a tap. In some embodiments, the tap used is a 4.75 mm tap.

Figure 6:
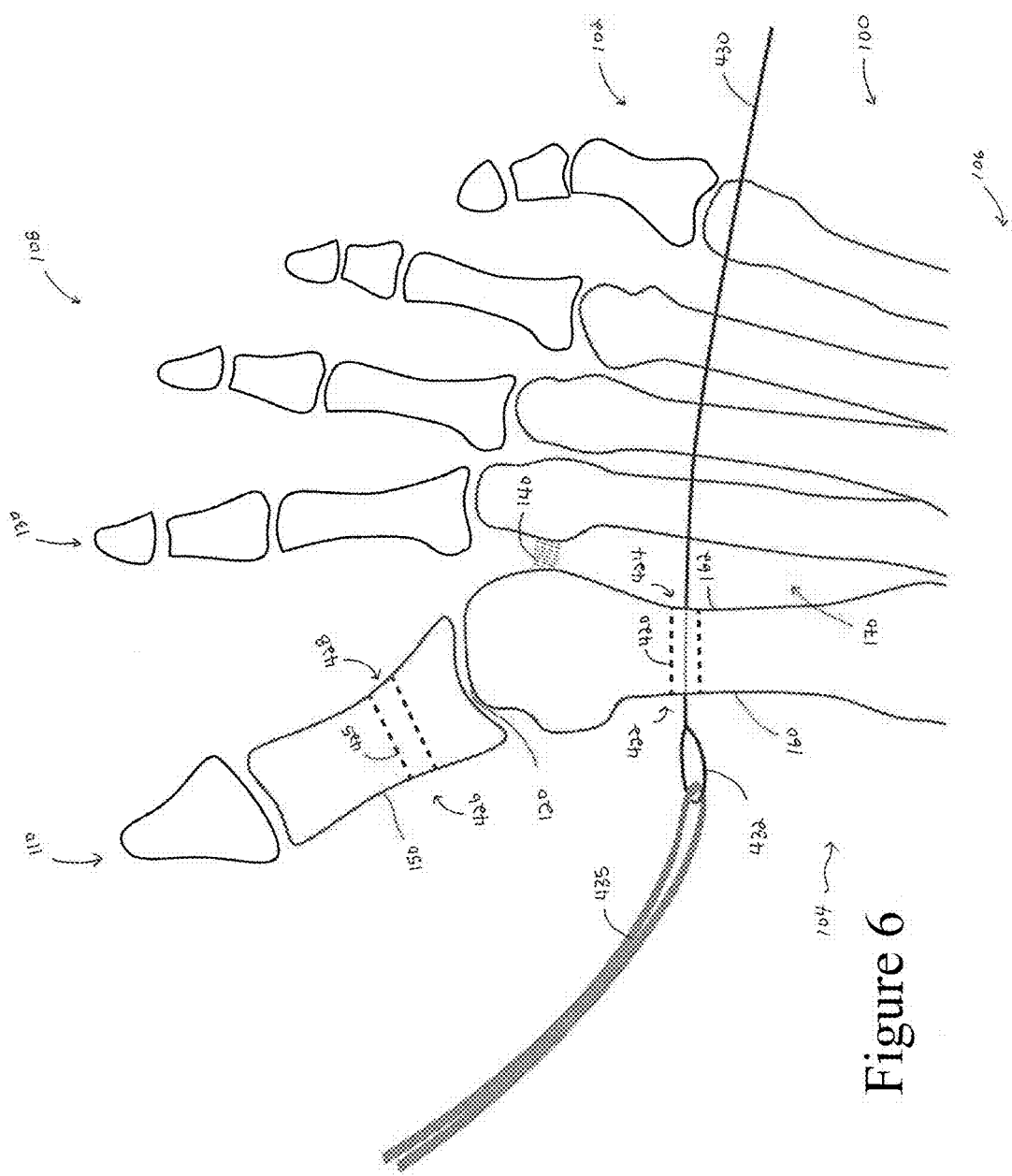
FIG. 6 illustrates a top view of the superior-anterior cross-sectional view of the foot with hallux varus of FIGS. 3-5, illustrating threading a suture passer through the first hole.
Figure 7:
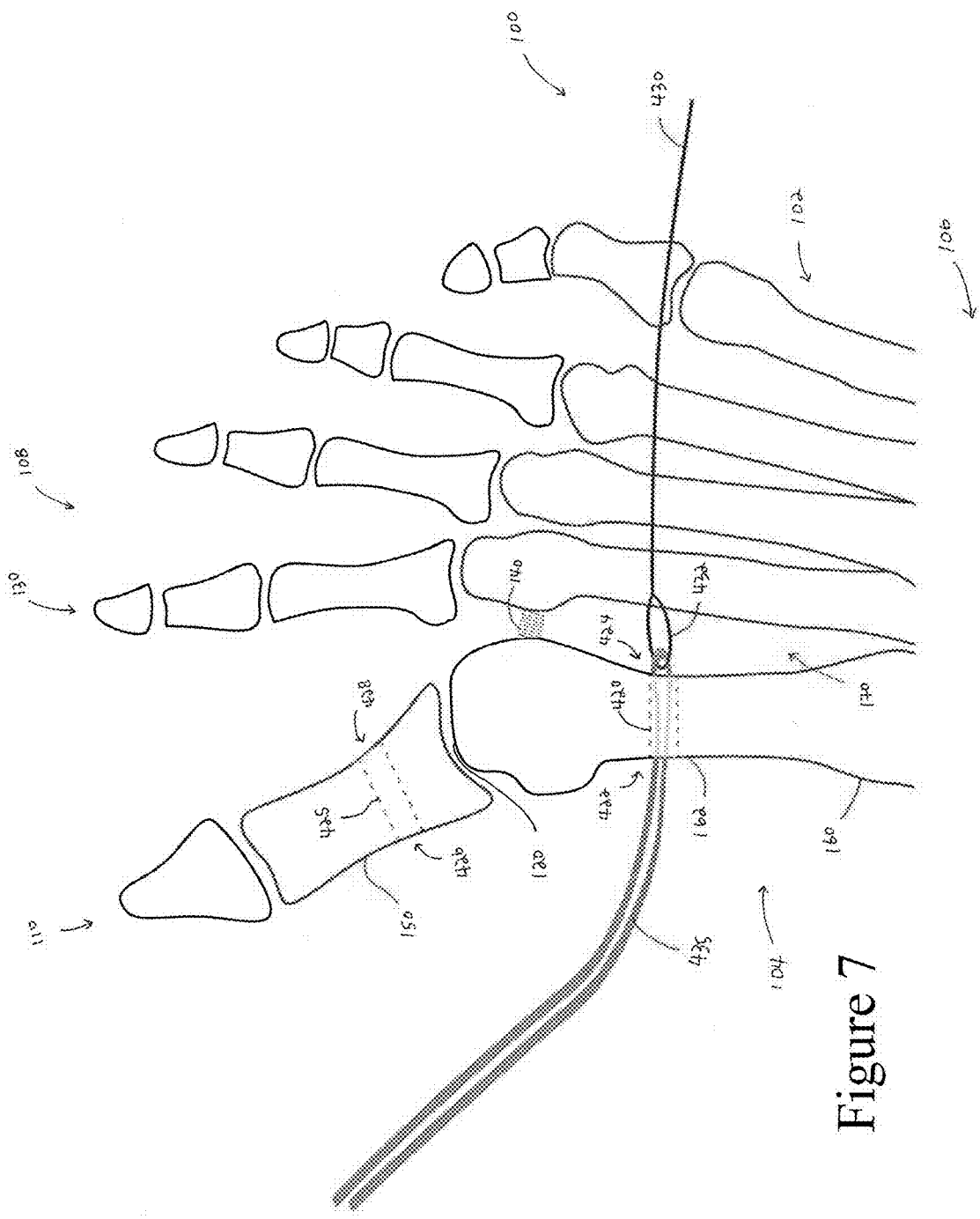
FIG. 7 illustrates a top view of the superior-anterior cross-sectional view of the foot with hallux varus of FIGS. 3-6, illustrating pulling a suture tape engaged to the suture passer through the first hole.

The method for treating hallux varus 300 can include block 340 describing threading a suture passer through the first hole and pulling a suture tape through the first hole. As illustrated in FIG. 6, the method for treating hallux varus 300 can use a suture passer 430 to thread a suture tape 435 through the first hole 420. In some embodiments, the suture passer 430 can include an engagement portion 432 that can engage and retain a portion of the suture tape 435. In some examples, the engagement portion 432 can removably retain a portion of the suture tape 435. In some examples, the suture tape 435 is double-stranded and is looped through the engagement portion 432. As illustrated in FIG. 6, the long end of the suture passer 430 is threaded through the first hole 420. FIG. 7 illustrates the suture passer 430 being pulled through the first hole 420 from the medial end 422 to the lateral end 424 and into the first interspace 170. As the suture passer 430 is pulled through, the attached suture tape 435 can be pulled through the first hole 420 from the medial side 104 of the foot 100 and into the first interspace 170.

Figure 8:
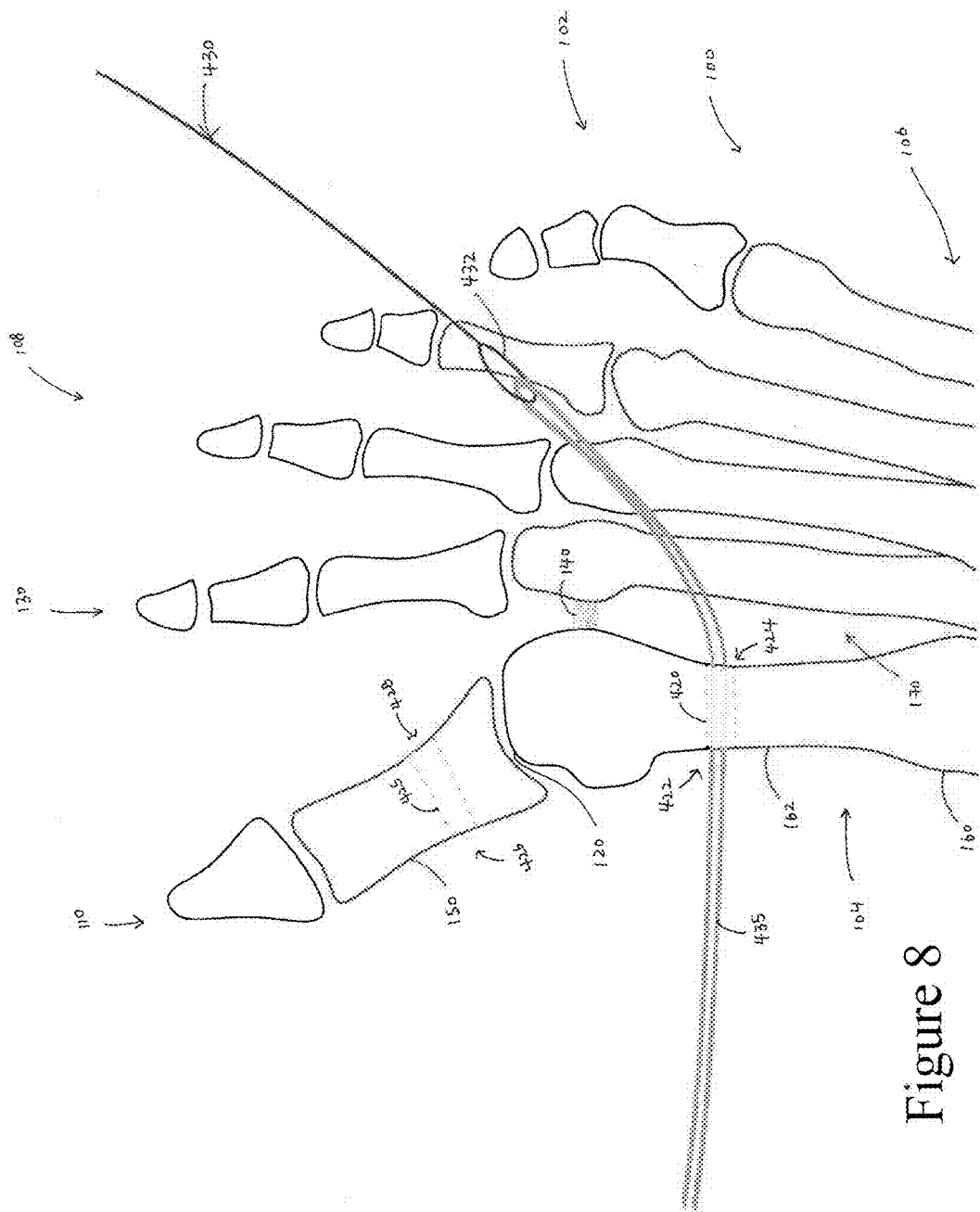
FIG. 8 illustrates a top view of the superior-anterior cross-sectional view of the foot with hallux varus of FIGS. 3-7, illustrating pulling the suture passer and the attached suture tape along a lateral side of the first metatarsal phalangeal joint to the second hole.
Figure 9:
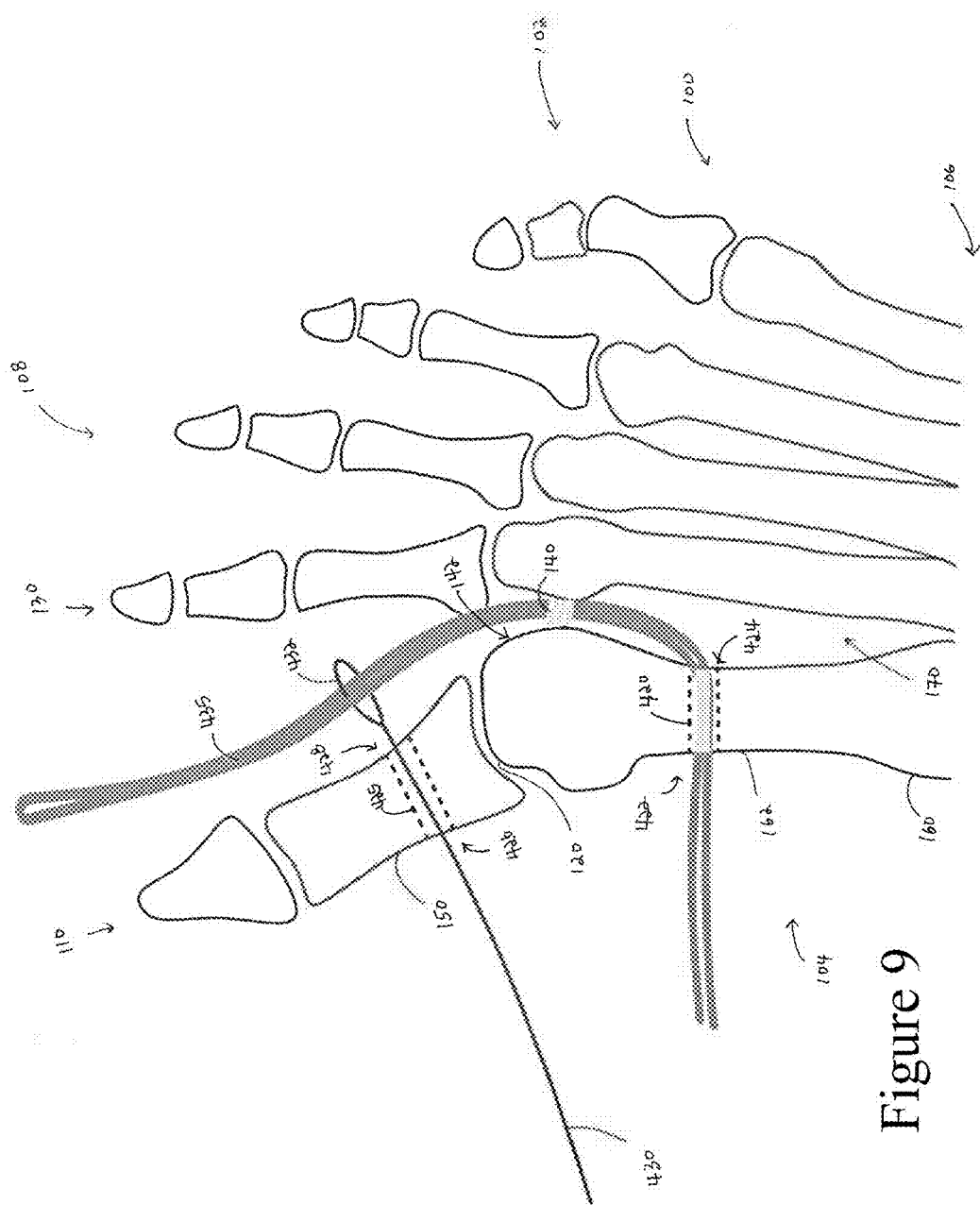
FIG. 9 illustrates a top view of the superior-anterior cross-sectional view of the foot with hallux varus of FIGS. 3-8, illustrating threading the suture passer through the second hole.

In some embodiments, the method for treating hallux varus 300 can include block 350 describing pulling the suture passer and the attached suture tape along a lateral side of the first metatarsal phalangeal joint to the second hole. As illustrated in FIG. 8, in some embodiments the suture passer 430 can continue to pull the engaged suture tape 435 from the first interspace 170 in a distal direction 108. In some examples, as shown in FIG. 9, the suture tape 435 can be pulled alongside the lateral side 142 of the first metatarsal 160 to the lateral side 102 of the hallux.

Figure 10:
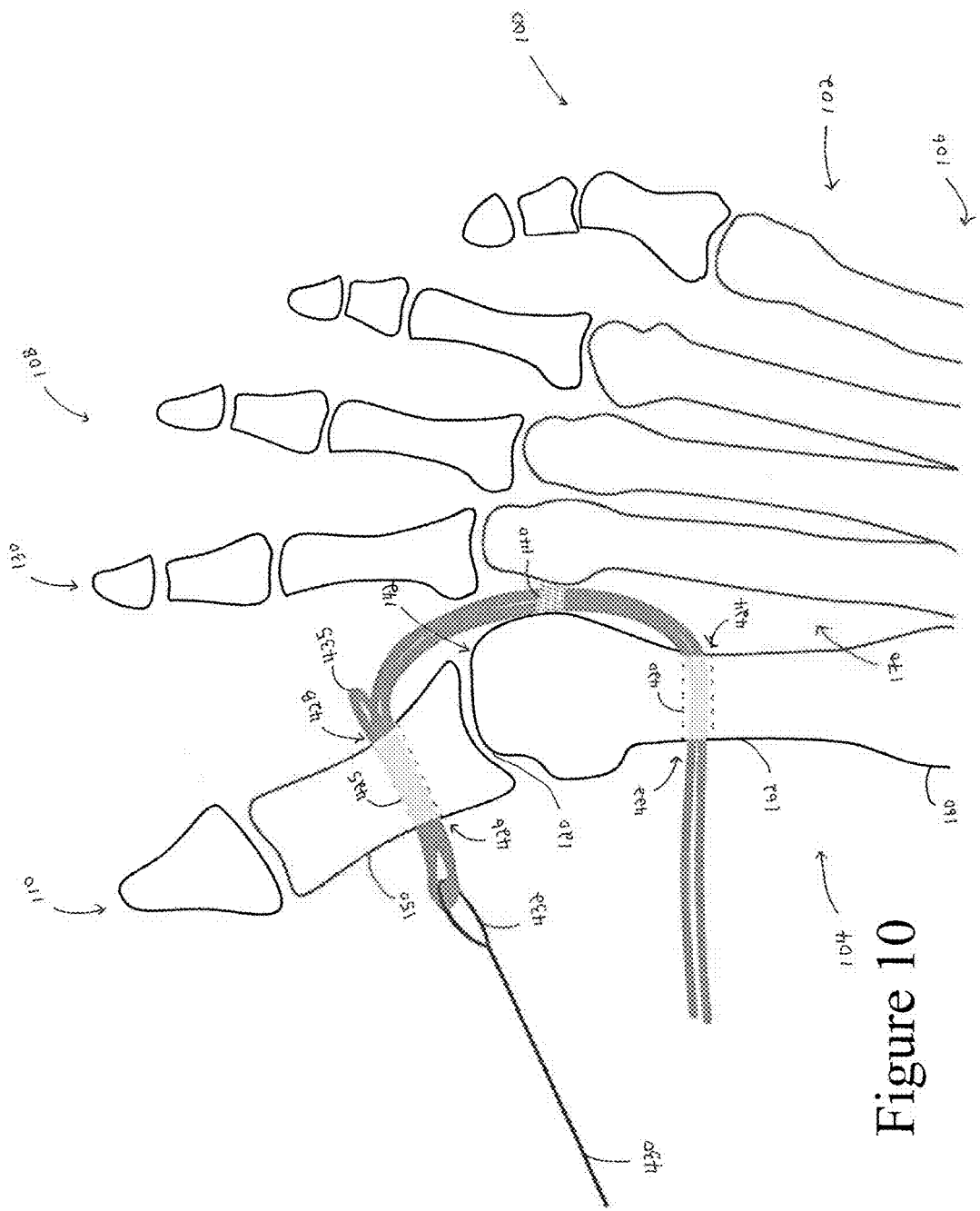
FIGS. 10-11 illustrate a top view of the superior-anterior cross-sectional view of the foot with hallux varus of FIGS. 3-9, illustrating pulling the suture tape through the second hole.
Figure 11:
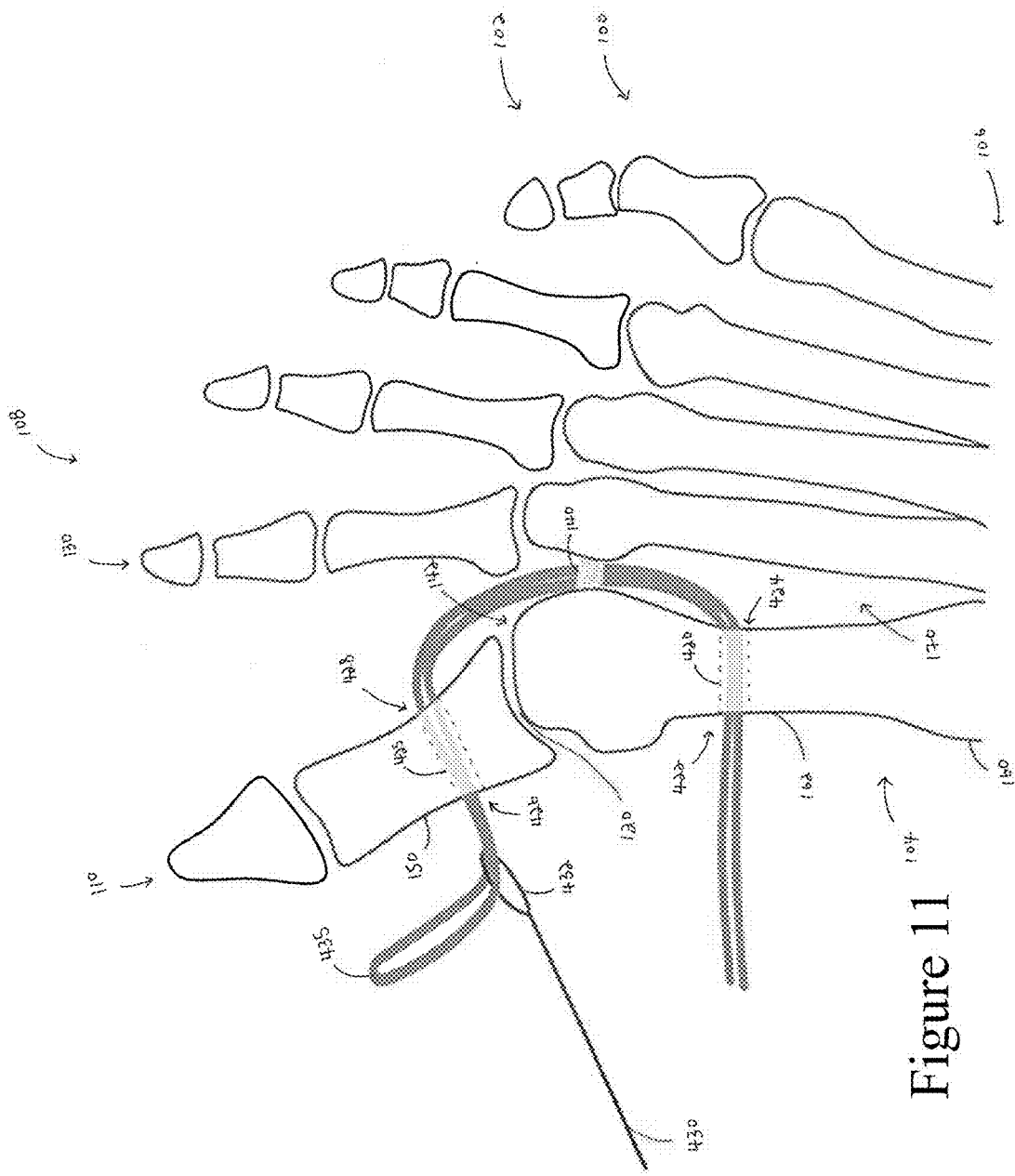

In some embodiments, the method for treating hallux varus 300 can include block 355 that describes threading the suture passer through the second hole and pulling a suture tape through the second hole. Turning once again to FIG. 9, the narrow end of the suture passer 430 can be inserted into the lateral side 102 of the second hole 425. In some embodiments, the suture passer 430 can be inserted from the lateral end 428 such that the suture passer 430 exits from the medial end 426. As shown in FIGS. 10-11, the suture passer 430 can be pulled through the second hole 425 and out of the medial end 426. In some examples, this can pull the suture tape 435 through the second hole 425 such that the free ends of the suture tape 435 are exiting the medial side 104 of the second hole 425.

In some examples, the method for treating hallux varus 300 can include block 360 that describes tensioning the suture tape such that the suture tape is placed longitudinally along the lateral side of the metatarsal phalangeal joint. As shown in FIGS. 9-11, in some examples, the suture tape 435 can be pulled from the lateral end 424 of the first hole 420 to the lateral end 428 of the second hole 425. In some examples, the suture tape 435 can be tensioned and adjacent to the lateral side 142 of the first metatarsal phalangeal joint 120.

As noted above, although the method for treating hallux varus 300 describes threading the suture passer 430 and the attached suture tape 435 in a distal direction from the first hole 420 in the first metatarsal 160 to the second hole 425 in the proximal phalanx 150, the direction the suture passer 430 and the attached suture tape 435 are pulled is not important. For example, the suture passer 430 and the attached suture tape 435 can instead be pulled in a proximal direction from the hole 425 in the proximal phalanx 150 to the hole 420 in the first metatarsal 160.

Figure 12:
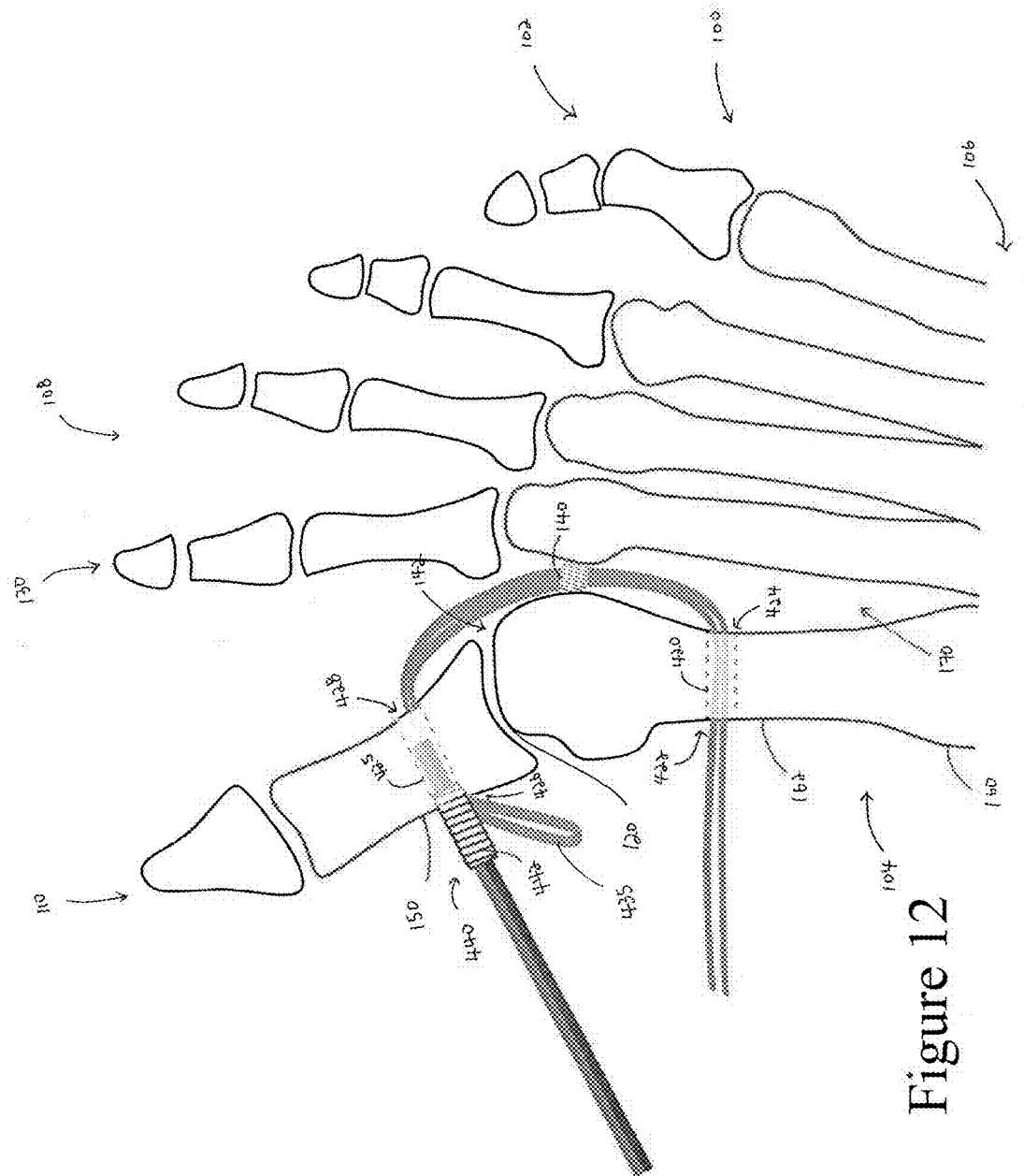
FIGS. 12-13 illustrate a top view of the superior-anterior cross-sectional view of the foot with hallux varus of FIGS. 3-11, illustrating threading a first interference screw into the second hole.
Figure 13:
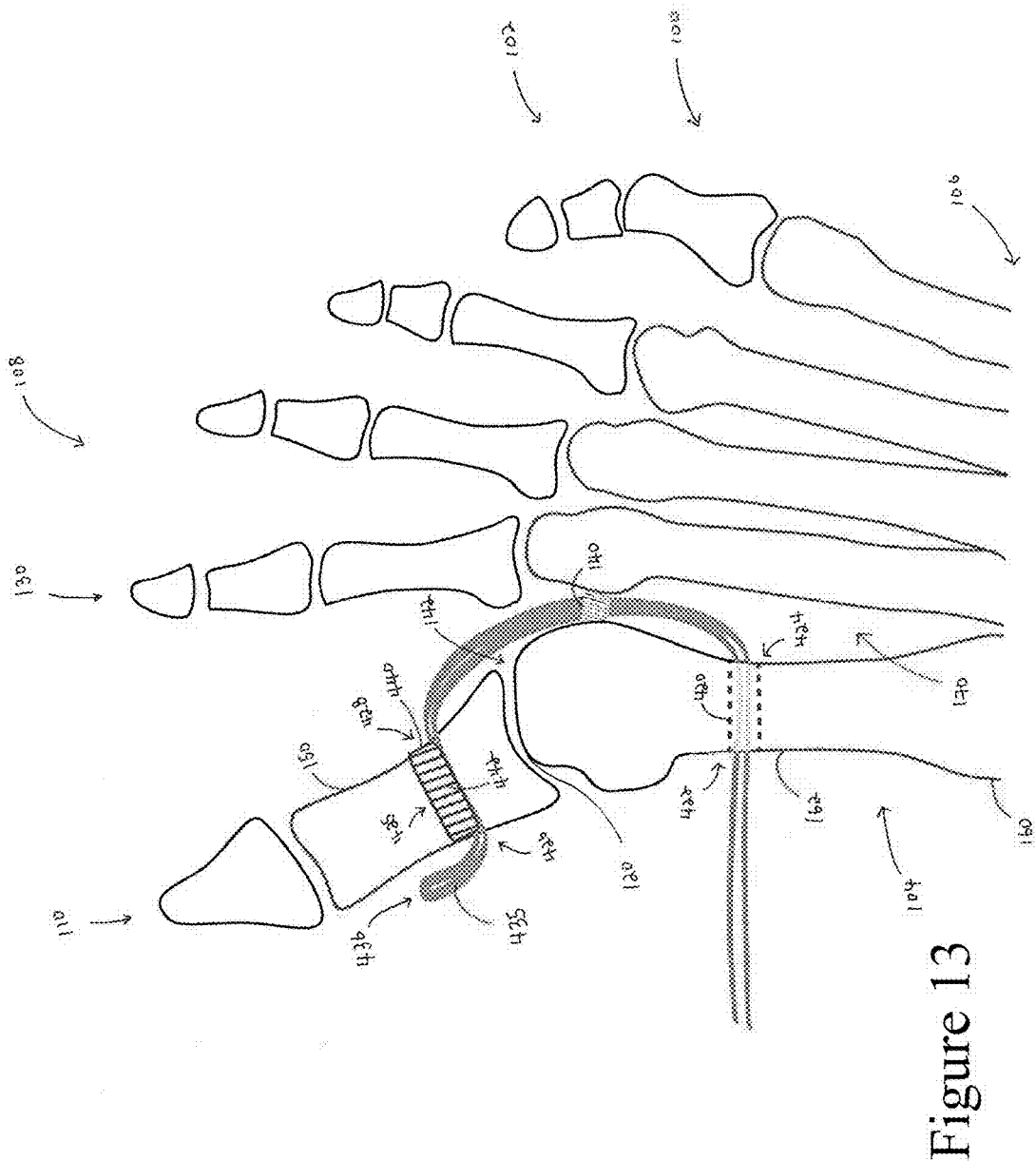

In some embodiments, the method for treating hallux varus 300 can include block 360 that describes threading a first interference screw into either the first hole or the second hole. As illustrated in FIG. 12, in some examples, the first interference screw 440 can be threaded into the second hole 425. In some embodiments, the first interference screw 440 can be driven into the second hole 425 from the medial end 426 to the lateral end 428. In some examples, the first interference screw 440 can have an external thread 445 that can engage the medial and lateral cortices. As shown in FIG. 13, as the first interference screw 440 is screwed into the second hole 425, the external thread 442 engages and secures the portion of the suture tape 435 that has been pulled through the second hole 425. In some examples, the first interference screw 440 is a 4.75 mm PEEK interference screw.

Figure 14:
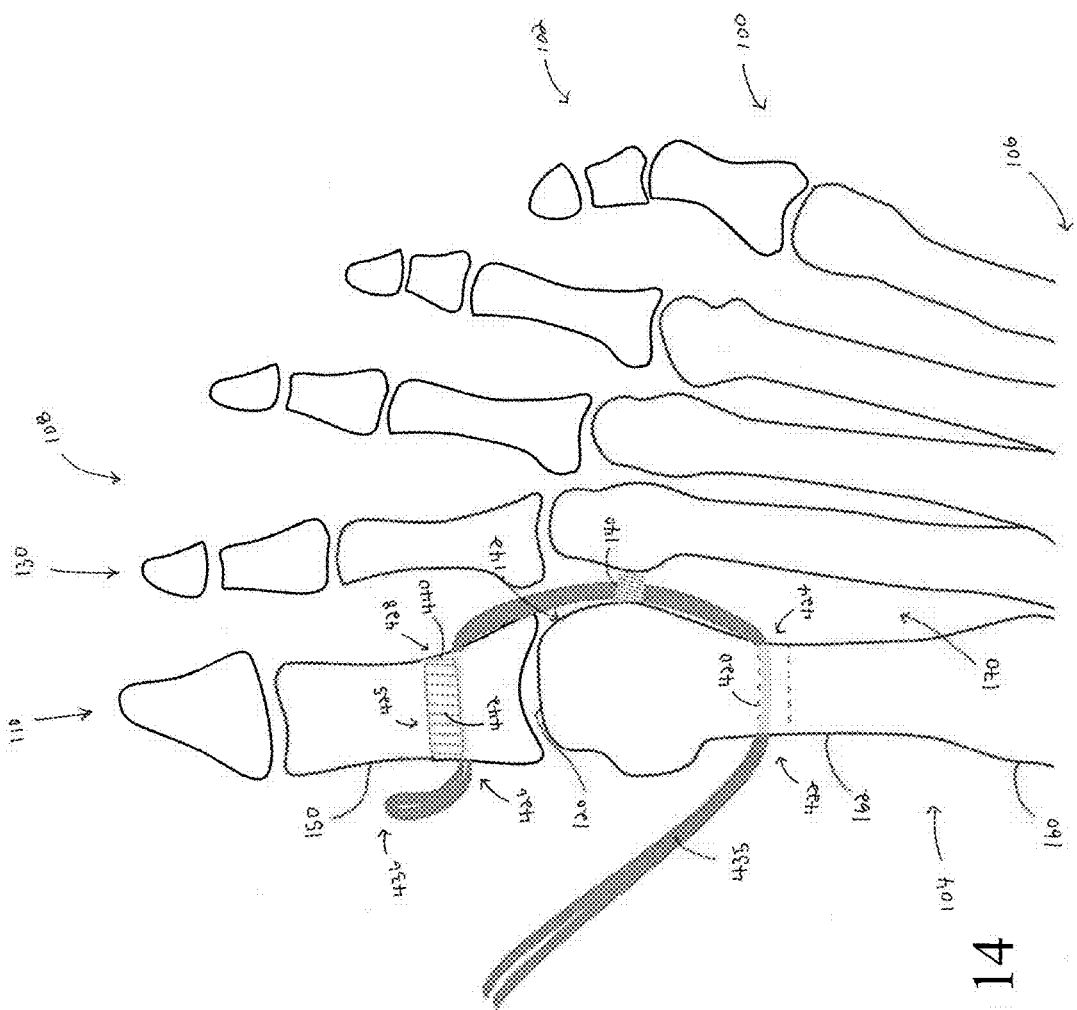
FIG. 14 illustrates a top view of the superior-anterior cross-sectional view of the foot with hallux varus of FIGS. 3-13, illustrating reducing the hallux to a rectus position relative to the first metatarsal.

In some examples, the method for treating hallux varus 300 can include block 365 that describes reducing the hallux to a rectus position relative to the first metatarsal. As shown in FIG. 14, in some examples, the hallux varus 110 deformity can be manually reduced to a rectus position relative to the first metatarsal 160. In some embodiments, the portion of the suture tape 435 exiting from the medial side 104 of the first hole 420 is maximally tensioned.

Figure 15:
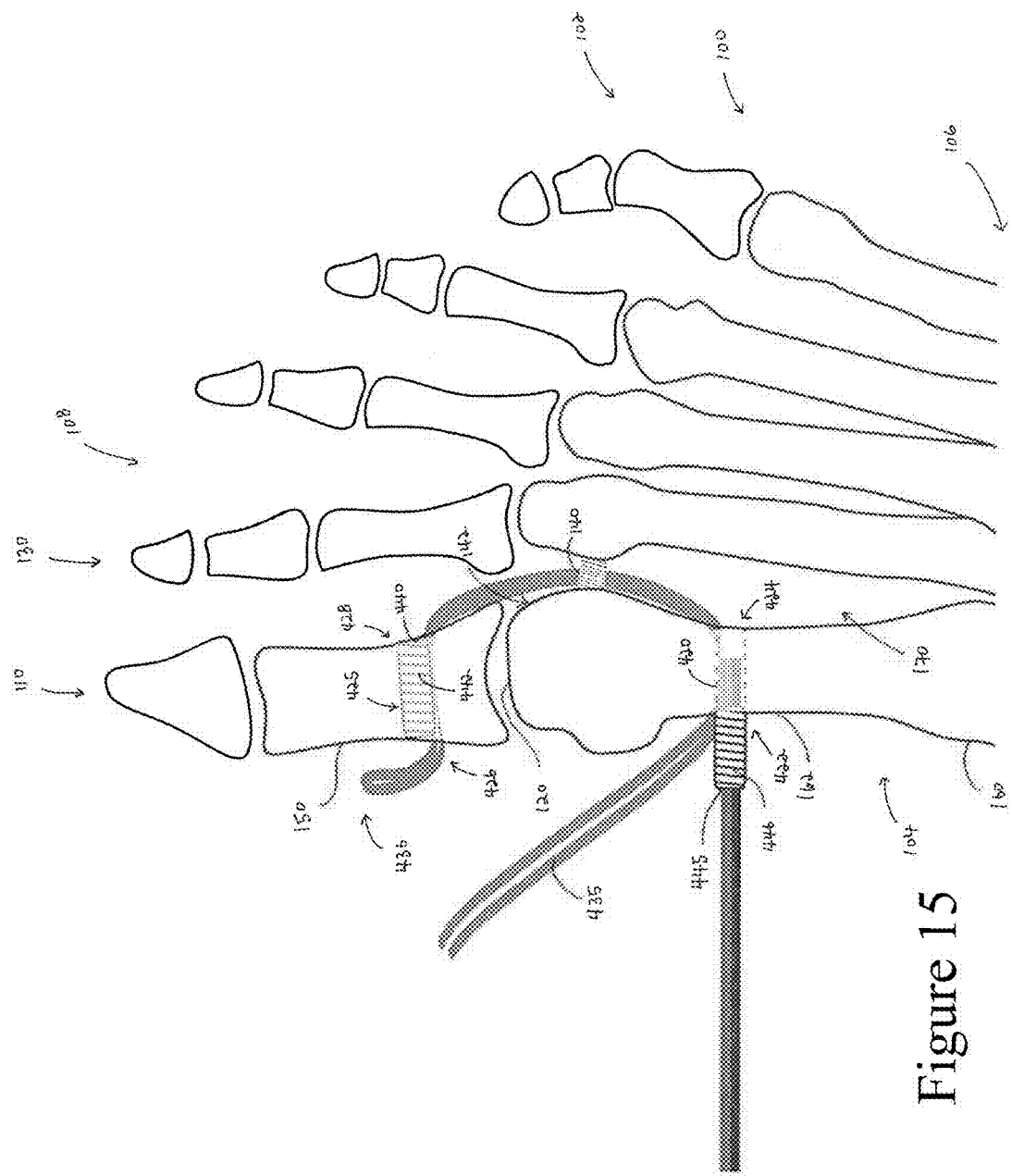
FIGS. 15-16 illustrate a top view of the superior-anterior cross-sectional view of the foot with hallux varus of FIGS. 3-14, illustrating threading a second interference screw into the first hole.
Figure 16:
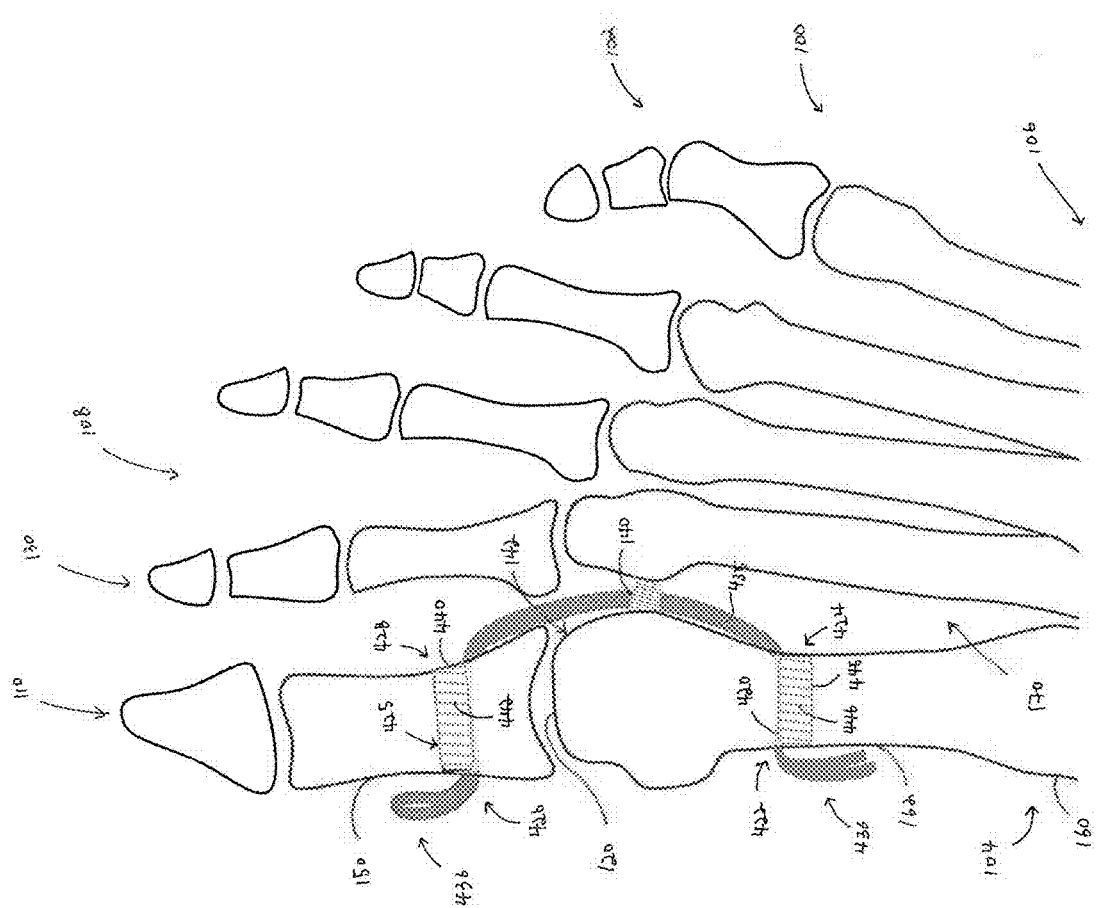

In some embodiments, the method for treating hallux varus 300 can include block 370 that describes threading a second interference screw into the second of the first hole or the second hole. As illustrated in FIG. 15, in some examples, the second interference screw 445 can be threaded into the first hole 420. In some embodiments, the first hole 420 can be driven into the first hole 420 from the medial end 422 to the lateral end 424. In some examples, the second interference screw 445 can have an external thread 446 that can engage the medial and lateral cortices. As shown in FIG. 16, as the second interference screw 445 is screwed into the first hole 420, the external thread 446 engages and secures the portion of the suture tape 435 that has been pulled through the first hole 420. In some examples, the second interference screw 445 is a 4.75 mm PEEK interference screw.

Figure 17:
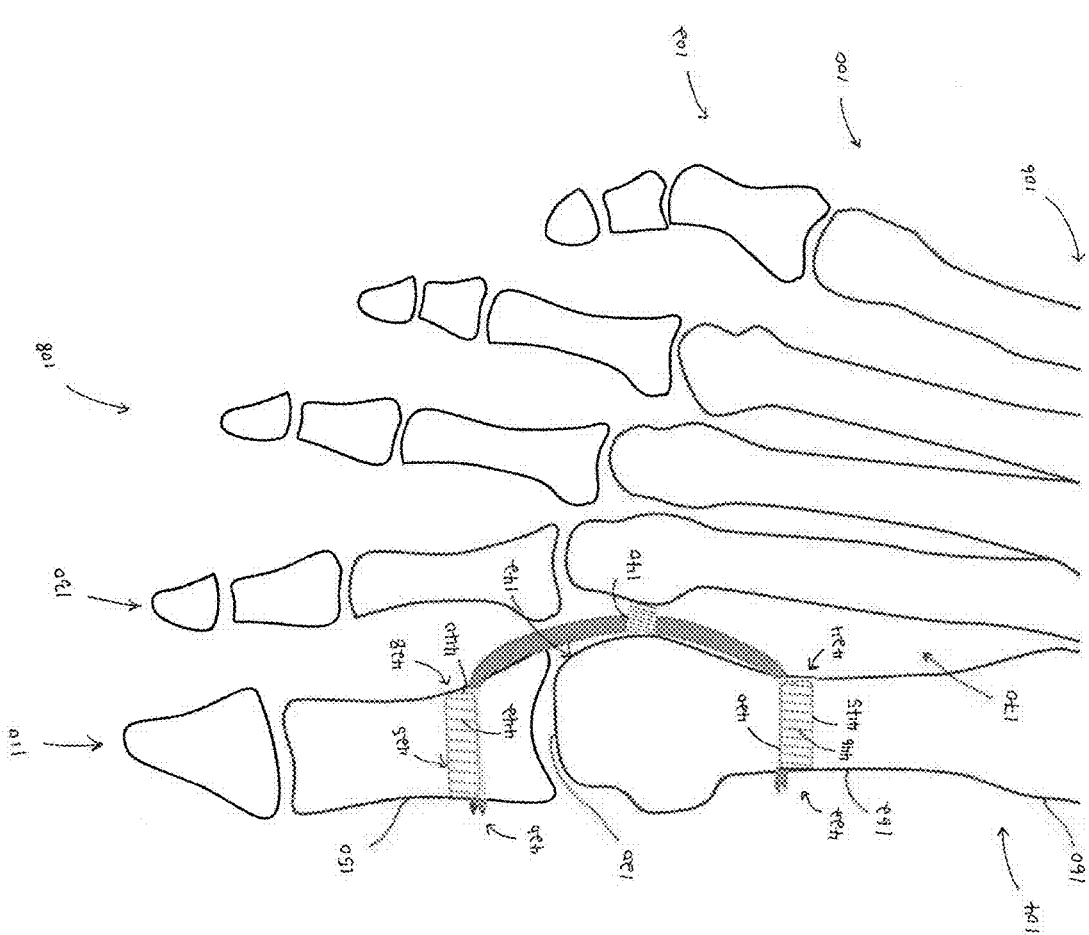
FIG. 17 illustrates a top view of the superior-anterior cross-sectional view of the foot with hallux varus of FIGS. 3-16, illustrating removing the remaining ends of the suture tape.

In some examples, the method for treating hallux varus 300 can include block 375 that describes removing the remaining ends of the suture tape. As shown in FIG. 16, once the first interference screw 440 and the second interference screw 445 have been inserted, the ends 436 of the suture tape 435 can extend from the medial side 104 of the foot. In some embodiments, as shown in FIG. 17, these ends 436 can be removed.

As noted above, although the method for treating hallux varus 300 describes placing the first interference screw 440 in the second hole 425 and the second interference screw 445 in the first hole 420, the order in which the two interference screws are placed is not important. For example, the first interference screw 440 can instead be threaded into the first hole 420 and the second interference screw 445 in the second hole 425.

Figure 18:
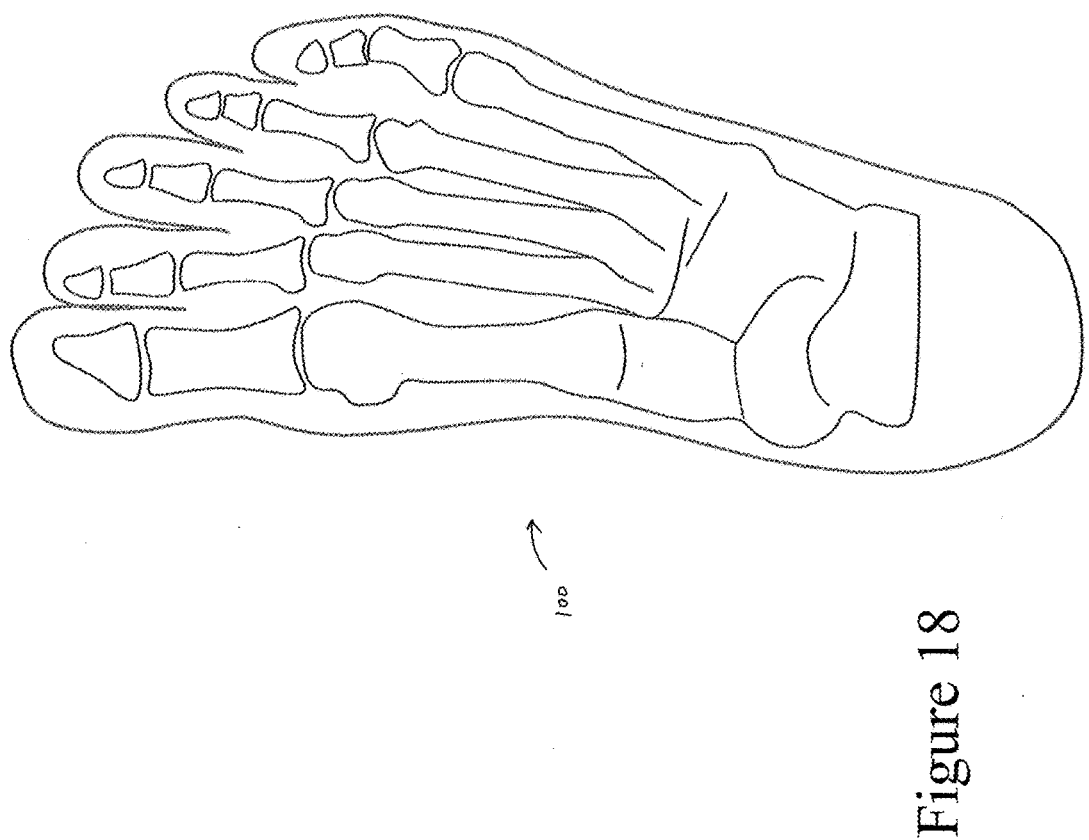
FIG. 18 illustrates a top view of the superior-anterior cross-sectional view of the foot with hallux varus of FIGS. 3-17, after the foot is treated, using the methods described in FIGS. 2A-2B.

Once the second interference screw 445 is placed, the first interference screw 440 in the proximal phalanx 150 and the second interference screw 445 in the first metatarsal 160 firmly fix the suture tape 435 across the first metatarsal phalangeal joint 120 longitudinally, as well as within each bone. In some examples, this can provide a knotless, buttonless fixation of suture tape 435 into the respective bones about the first metatarsal phalangeal joint 120. As illustrated in FIG. 18, the described method can correct the hallux varus.

As discussed extensively above, the method for treating hallux varus 300 can be equally performed by passing the suture tape 435 from distal to proximal or proximal to distal, and also by placing the interference screw into the proximal hole first, or the distal hole first, without any difference in the reduction of the deformity or surgical outcome. The proximal to distal, or distal to proximal sequence is based purely on surgeon preference and the order is inconsequential to the overall technique.

In some embodiments, the method for treating hallux varus can include any combination of the steps described in method for treating hallux varus 300. Turning back to FIG. 2A, in some embodiments, the method for treating hallux varus 200 can include only four steps. In some examples, the method for treating hallux varus 200 includes block 210 that describes forming a first hole in a first metatarsal of the foot. As described above and illustrated in FIG. 4, the first hole 420 can be formed in the first metatarsal 160. In some examples, the first hole 420 can be formed in the medial side of the first metatarsal 160 such that the first hole 420 is drilled from a medial end 422 to a lateral end 424. In some embodiments, the first hole 420 is made using a cannulated drill 450 with a drill head 452. In some examples, a 4.00 mm cannulated drill 450 can used.

In some embodiments, the method for treating hallux varus 200 can include block 220 that describes forming a second hole in a proximal phalanx of a hallux of the foot. As described above and illustrated in FIG. 5, the second hole 425 can be formed in the proximal phalanx 150. In some examples, the second hole 425 can be formed in the medial side of the proximal phalanx 150 such that the second hole 425 is drilled from a medial end 426 to a lateral end 428. In some embodiments, the second hole 425 is drilled from a medial end 426 to a lateral end 428. In some embodiments, the second hole 425 is made using a cannulated drill 450 with a drill head 452. In some examples, a 4.00 mm cannulated drill 450 can be used.

In some examples, the method for treating hallux varus 200 can include block 230 that describes passing a suture through the first hole, along a lateral side of a first metatarsal phalangeal joint, and through the second hole. As described above and illustrated in FIGS. 6-11, in some embodiments, the suture tape 435 can be passed through the first hole 420, along the lateral side 102 of the first metatarsal phalangeal joint 120. In some examples, the suture tape 435 can then be passed through the second hole 425. In some examples, the suture tape 435 can be pulled such that it is adjacent to the lateral side 142 of the first metatarsal phalangeal joint 120. In some embodiments, the suture tape 435 can be passed from a medial side 104 to a lateral side 102 of the first hole 420. In some embodiments, the suture tape 435 is passed from a lateral side 102 to the medial side 104 of the second hole 425. In some examples, the suture tape 435 is pulled towards the distal end 108 of the foot.

In some embodiments, the method for treating hallux varus 200 can include block 240 that includes securely fixating the suture within the first hole and the second hole with a first interference screw inserted within the first hole and a second interference screw inserted within the second hole. As described above and illustrated in FIGS. 12-16, in some embodiments, an interference screws 440, 445 is inserted within the first hole 420 and a second interference screws 440, 445 is inserted within the second hole 425. In some examples, the interference screws 440, 445 have external threads 442, 446 that engage with the internal surface of the holes 420, 425 to secure the suture tape 435 that are extended through each of the holes 420, 425.

The present disclosure is not limited to the embodiments described above. Various changes and modifications can, of course, be made, without departing from the scope and spirit of the present invention. Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents. As used in the claims the conjunction "or" means the inclusive or (and/or, either element independently or any combination of the elements together).

What is claimed is:

1. A method of correcting hallux varus joint deformity, comprising:
    forming a first hole in a first metatarsal of a foot, wherein the first hole extends from a medial side of the first metatarsal to a lateral side of the first metatarsal;
    forming a second hole in a proximal phalanx of a hallux of the foot, wherein the second hole extends from a medial side of the proximal phalanx to a lateral side of the proximal phalanx;
    passing a suture through the first hole, along a lateral side of a first metatarsal phalangeal joint, and through the second hole; and
    securely fixating the suture within the first hole and the second hole with a first interference screw inserted within the first hole and a second interference screw inserted within the second hole,
    wherein the suture is tensioned between the first and second holes to reduce the hallux to a rectus position relative to the first metatarsal.

2. The method of claim 1, wherein the first hole is formed before the second hole.

3. The method of claim 1, wherein the second hole is formed before the first hole.

4. The method of claim 1, wherein the suture is passed first through the first hole and then through the second hole.

5. The method of claim 1, wherein the suture is passed first through the second hole and then through the first hole.

6. The method of claim 1, comprising using one or more suture passers to pass the suture through the first hole, along the lateral side of the first metatarsal phalangeal joint, and through the second hole.

7. The method of claim 1, wherein the interference screws extend in a medial-to-lateral direction through the first and second holes, with threads of the first and second interference screws engaging medial and lateral cortices of the first metatarsal and the proximal phalanx, respectively.

8. A method of correcting hallux varus joint deformity, comprising:
    making a first incision medial or dorsomedial to a first metatarsal phalangeal joint;
    making a second incision between a hallux and a second toe of a foot, wherein the second incision is lateral to the first metatarsal phalangeal joint;
    driving a guidewire into a medial side of a first bone on a first side of the first metatarsal phalangeal joint,
        wherein the guidewire is driven from the medial side to a lateral side of the first bone, and
        wherein the first bone is either a first metatarsal and the guidewire is driven through a metatarsal neck, or wherein the first bone is a proximal phalanx of the hallux;
    drilling a first hole along the guidewire to form a medial to lateral hole in the medial side of the first bone, wherein the hole is formed using a 4.00 mm cannulated drill;
    driving a guidewire into a medial side of a second bone on a second side of the first metatarsal phalangeal joint,
        wherein the guidewire is driven from the medial side to a lateral side of the second bone, and
        wherein the second bone is either a first metatarsal and the guidewire is driven through a metatarsal neck, or wherein the second bone is a proximal phalanx of the hallux, the second bone being different from the first bone;
    drilling a second hole along the guidewire to form a medial to lateral hole in the medial side of the second bone, wherein the hole is formed using a 4.00 mm cannulated drill;
    tapping the first and second hole with a 4.75 mm tap;
    threading a suture passer through the first hole,
        wherein the suture passer retains a suture tape such that the suture tape is pulled through the first hole, and
        wherein the suture passer is threaded from the medial side to the lateral side of the first bone;
    pulling the suture passer and the attached suture tape along a lateral side of the first metatarsal phalangeal joint to the second hole;
    threading the suture passer through the second hole from the medial side to the lateral side of the second bone, and pulling the suture tape using the suture passer through the second hole from the lateral side to the medial side;
    tensioning the suture tape such that the suture tape is placed longitudinally along the lateral side of the metatarsal phalangeal joint;
    threading a first interference screw into either the first hole or the second hole to securely fixate the suture tape within either the first hole or the second hole, the first interference screw being driven from a medial end to a lateral end of the hole with screw threads engaging both medial and lateral cortices, wherein the first interference screw is a 4.75 mm interference screw;

reducing the hallux to a rectus position relative to the first metatarsal;

threading a second interference screw into the other of the first hole or the second hole to securely fixate the suture tape within the other of the first hole or the second hole while maintaining tension on the suture tape, the second interference screw being driven from a medial end to a lateral end of the hole, wherein the second interference screw is a 4.75 mm interference screw; and removing remaining ends of the suture tape.

* * * * *